US00PP25788P2

(12) United States Plant Patent
Meerow

(10) Patent No.: US PP25,788 P2
(45) Date of Patent: Aug. 4, 2015

(54) ***HIPPEASTRUM* PLANT NAMED 'BOCA'**

(50) Latin Name: ***Hippeastrum* hybrid**
Varietal Denomination: Boca

(71) Applicant: The United States of America, as represented by the Secretary of Agriculture, Washington, DC (US)

(72) Inventor: Alan W Meerow, Davie, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 125 days.

(21) Appl. No.: 13/987,875

(22) Filed: Sep. 11, 2013

(51) Int. Cl.
*A01H 5/02* (2006.01)

(52) U.S. Cl.
USPC ..... Plt./402

(58) Field of Classification Search
USPC ..... Plt./402
CPC ..... A01H 5/025; A01H 5/02; A01H 5/00
See application file for complete search history.

*Primary Examiner* — Kent L Bell
(74) *Attorney, Agent, or Firm* — Gail E. Poulos; John D. Fado; Lesley Shaw

(57) ABSTRACT

A new and distinct tripolid (2n=33) *Hippeastrum* interspecific hybrid plant named 'Boca' particularly characterized by "butterfly" shape flowers, measuring approximately 13-14 cm and 15-16 cm long, approximately 12-13.5 cm and 14-15 cm wide laterally, approximately 14-16 cm and 16-18 cm wide dorsal-ventrally, The flowers are densely striated purple pink (approximately red purple RHS 57A) on their inner surfaces, with an irregular marginal white RHS 155D picotee and a faint white RHS 155D keel on the outer lateral segments; the outer surfaces are more lightly striated with infusions of green RHS 149B and maroon RHS 178B along the keels.

3 Drawing Sheets

Latin name of the genus and species of the plant claimed: 'Boca' is a new Amaryllis plant that is a *Hippeastrum* Herb.

Variety denomination: The Amaryllis plant claimed is of the variety denominated 'Boca', *Hippeastrum* hybrid Herb.

BACKGROUND OF THE INVENTION

The present invention is a new and distinct interspecific hybrid of *Hippeastrum* Herb., commonly known as amaryllis, a member of the family Amaryllidaceae, and is henceforth referred to by the cultivar name 'Boca'.

'Boca' originated as a cross made by the inventor in 2001 as part of a breeding program in Miami, Fla., USA. The objectives of the breeding program are to develop new amaryllis varieties with novel floral form and coloration and heat tolerance. The female parent is an F1 interspecific hybrid (*H. ambiguum*×*H. papilio* clone 4-16, unpatented). The pollen parent is an unpatented selection from the complex cross (*H. ambiguum*×*H. papilio*)×(*H. lapacense*×*H. papilio*) with the breeder's code 35-2.

The new cultivar was selected on the basis of its "butterfly" floral shape and unique color pattern. Over the course of seven years of evaluation, 'Boca' has shown excellent heat resistance, grown under ambient conditions in Miami, Fla. under 50% shade, and resistance to Red Scorch fungus (*Staganospora curtisii*).

Asexual reproduction of the new cultivar by twin-scale cuttings taken in a controlled environment in Miami, Fla. has shown that the unique features of this new amaryllis are stable and reproduced true to type in successive generations.

SUMMARY OF THE INVENTION

The following traits have been repeatedly observed and are determined to be the unique characteristics of 'Boca'. It is contrasted with its parents in Table 1. These characteristics in combination distinguish 'Boca' as a new and distinct cultivar:

1) "Butterfly" floral shape with faint white feels on the upper (adaxial) surface of the tepals.
2) 'Boca' shows resistance to Red Scorch fungus (*Staganospora curtisii*) and high temperatures, approximately 30-35° C., as do its parents.

TABLE 1

Comparison of *Hippeastrum* 'Boca' and its two parent plants.

| Characteristic | 'Boca' | Clone 4-16 | Clone 35-2 |
|---|---|---|---|
| No. scapes per season | 2-3 | 2-3 | 2 |
| Scape height (cm) | 35-45 | 50-55 | 55-60 |
| No. flrs. Per scape | 4 | 2-4 | 3-4 |
| Flr color | Deep pink | Red-purple on white | Burgundy on white |

Of the numerous commercial cultivars of amaryllis familiar to the inventor, the most similar to the new *Hippeastrum* 'Boca' is *Hippeastrum* 'Rio' (U.S. Pat. No. 12,633), from which 'Boca' differs by the broad lateral inner tepals that give the distinctive "butterfly" appearance to the flowers, and the lack of floral fragrance.

BRIEF DESCRIPTION OF THE PHOTOGRAPHS

DETAILED BOTANICAL DESCRIPTION

The cultivar Boca has not been observed under all possible environmental conditions. The phenotype may vary somewhat with variations in environment such as temperature, daylength and light intensity, without, however, any variance in genotype.

Color descriptions below are based on evaluations with a Minolta CR-400 colorimeter at CIE D65/2$^0$ illumination/viewer conditions. The color parameters correspond to the uniform color space CIELAB, derived from Gonnet (Journal of Horticultural Science, Volume 68, 499-510, 1993; Food Chemistry, Volume 63, 409-415, 1998). Two color coordinates, a* and b*, as well as a psychometric index of lightness, L*, are defined. The L* is a measurement of luminosity, i.e., the equivalence of each color on the gray scale, ranging from 0 (black) to 100 (white). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts (Ayala-Silva and Meerow, Proc. Int. Trop. Hort. Soc., Volume 50, 138-144, 2006). The colorimeter takes three consecutive measurements of each sample, which was repeated three times, thus each set of color coordinates obtained are means of nine measurements. Where a reasonably close match could be discerned, The R.H.S. Colour Chart (Royal Horticultural Society, 1966) is also referenced.

TABLE 2

Colorimeter readings under the CIELAB color space for various locations on the flowers of *Hippeastrum* hybrid 'Boca'. See text for explanation of the values.

Figure 1B:
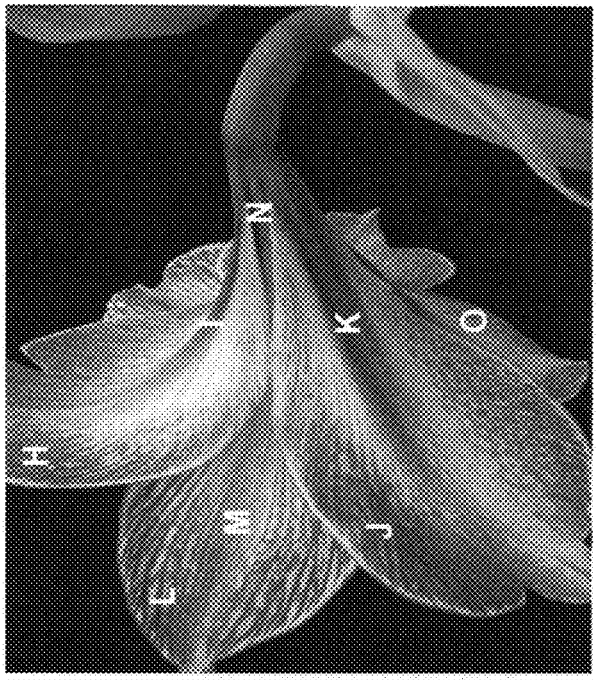
FIG. 1A and FIG. 1B are gray scale pictures of the flowers of *Hippeastrum* hybrid 'Boca' showing the locations of colorimeter readings in Table 2.
Figure 1A:
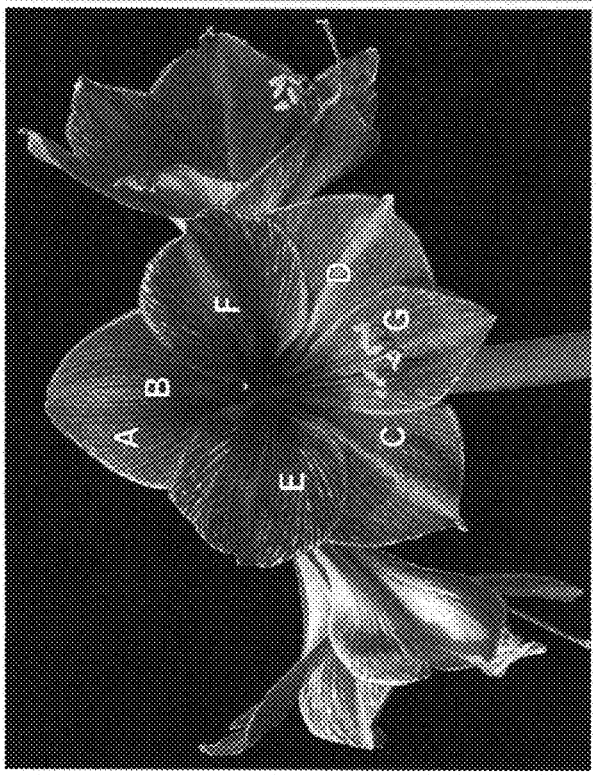
Figure 2:
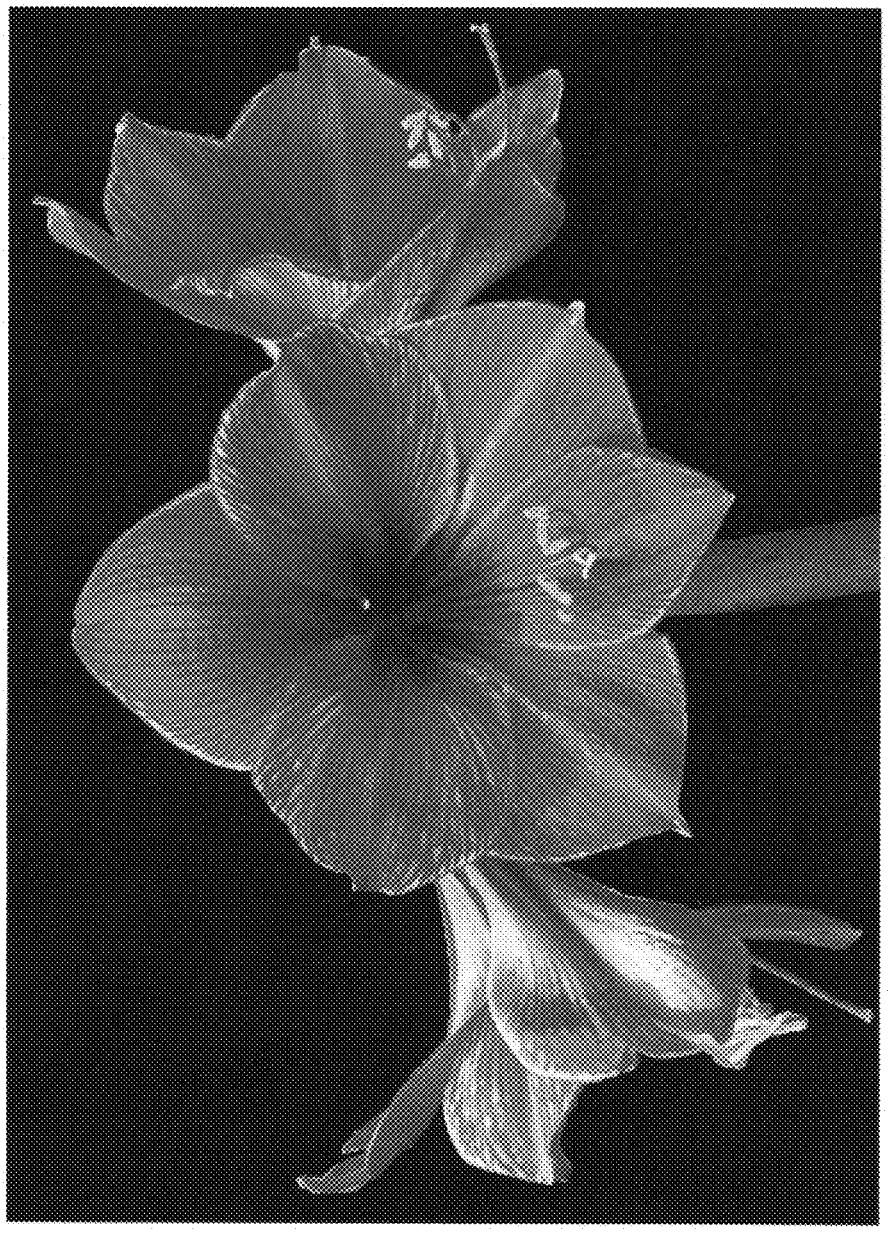
FIG. 2 and FIG. 3 are color photographs of the flower of *Hippeastrum* hybrid 'Boca'.
Figure 3:
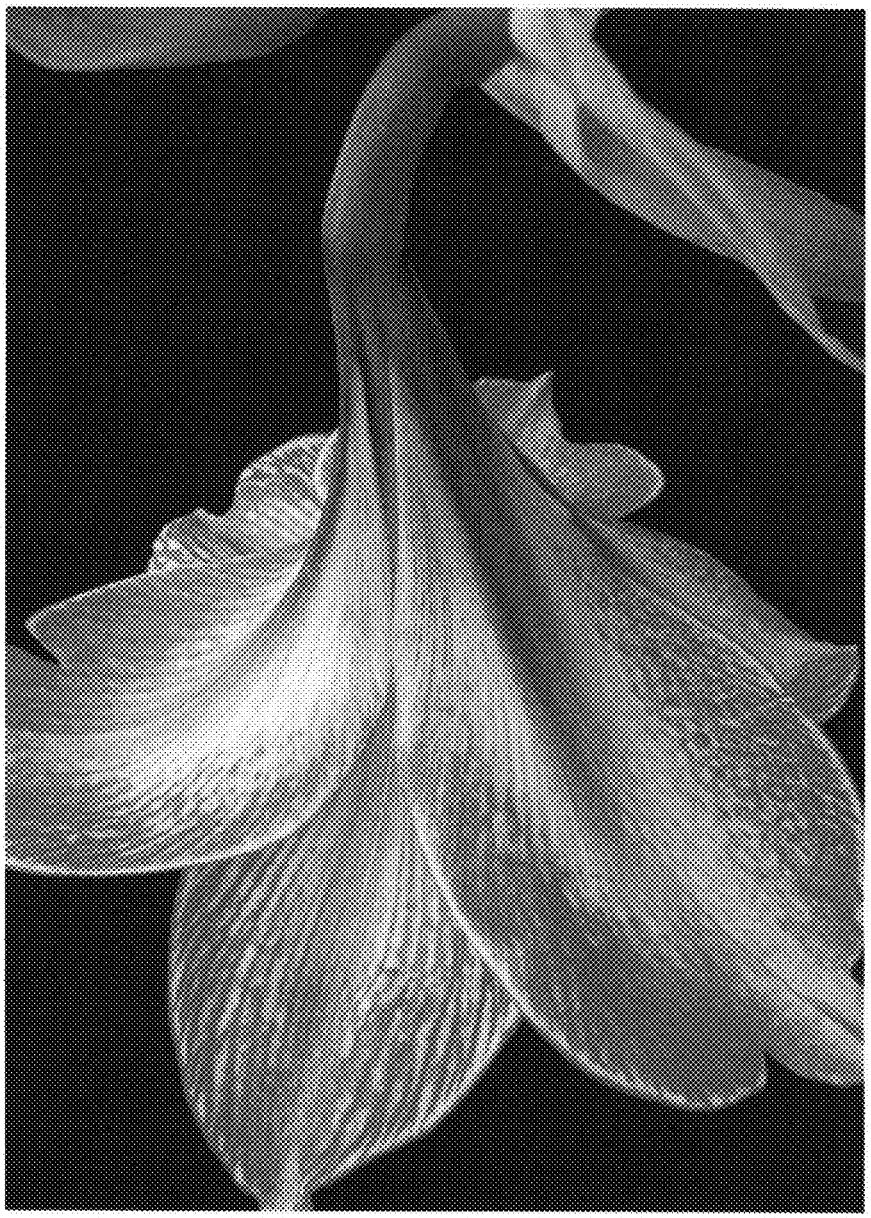

| Location (see FIG. 1) | | L*(C) | a*(C) | b*(C) |
|---|---|---|---|---|
| A | MEAN | 43.42 | 58.41 | 20.88 |
| | SD | 1.11 | 2.74 | 1.67 |
| B | MEAN | 44.34 | 52.70 | 19.12 |
| | SD | 0.07 | 0.04 | 0.09 |
| C | MEAN | 48.47 | 58.35 | 19.45 |
| | SD | 3.40 | 4.42 | 0.92 |
| D | MEAN | 59.64 | 27.15 | 9.44 |
| | SD | 0.87 | 0.82 | 0.25 |
| E | MEAN | 47.16 | 59.76 | 20.28 |
| | SD | 0.52 | 0.21 | 0.55 |
| F | MEAN | 47.92 | 56.07 | 15.14 |
| | SD | 0.05 | 0.07 | 0.08 |
| G | MEAN | 55.97 | 50.04 | 15.83 |
| | SD | 3.35 | 4.69 | 1.35 |
| H | MEAN | 51.49 | 46.51 | 14.71 |
| | SD | 2.84 | 11.72 | 0.69 |
| I | MEAN | 61.57 | 32.34 | 10.86 |
| | SD | 0.05 | 0.20 | 0.09 |
| J | MEAN | 55.29 | 45.34 | 12.15 |
| | SD | 1.92 | 5.03 | 0.98 |
| K | MEAN | 68.19 | 9.64 | 20.27 |
| | SD | 0.05 | 0.05 | 0.03 |
| L | MEAN | 56.49 | 38.66 | 12.93 |
| | SD | 4.32 | 11.33 | 1.59 |
| M | MEAN | 58.43 | 42.01 | 7.42 |
| | SD | 0.06 | 0.04 | 0.02 |
| N | MEAN | 46.43 | 30.65 | 14.05 |
| | SD | 0.06 | 0.09 | 0.05 |
| O | MEAN | 67.38 | 27.30 | 9.25 |
| | SD | 3.77 | 6.77 | 1.63 |

Botanical classification: *Hippeastrum* hybrid cultivar Boca.

Parentage:

*Female or seed parent.*—Proprietary selection of *Hippeastrum ambiguum*×*H. papilio* identified as code number 4-16, not patented.

*Male or pollen parent.*—(*H. ambiguum*×*H. papilio*)×(*H. lapacense*×*H. papilio*) with the breeder's code 35-2.

Propagation:

*Type.*—Twin-scale cuttings (division of the mother bulb into vertical segments and twin-scale units).

*Time to initiate roots, summer.*—About 30 days at temperatures of approximately 30° C.

*Time to initiate roots, winter.*—About 40 days at temperatures of approximately 22° C.

*Time to develop roots, summer.*—About 65 days at temperatures of approximately 30° C.

*Time to develop roots, winter.*—About 90 days at temperatures of approximately 22° C.

Plant description:

*Appearance.*—Perennial herbaceous amaryllis. Upright and clumping growth habit, moderately tall.

*Crop time.*—From bulb scale cuttings, about two years are required to produce a finished, flowering plant in a 15 to 20-cm container.

*Vigor.*—Moderately vigorous.

*Plant height.*—About 60 cm.

*Plant spread.*—About 70 cm.

Roots: White; numerous; fine and fibrous to moderately thick and fleshy; produced from basal plate of bulb; freely branching.

Bulb:

*Diameter.*—About 5-6 cm, increasing to about 8-9 with age.

*Circumference.*—About 18-19 cm, increasing to about 28 cm.

*Shape.*—Ovoid.

*Color.*—RHS 149A; tunic, RHS 165A.

*Offsets produced per year.*—One to two offsets per bulb.

Foliage description:

*Arrangement.*—Distichous.

*Quantity.*—About 4-8 per bulb.

*Length, mature leaves.*—About 44-71 cm.

*Width, mature leaves.*—About 3.5-5.5 cm.

*Shape.*—Lorate.

*Apex.*—Obtuse.

*Margin.*—Entire.

*Texture.*—Coarse; glabrous.

*Color.*—Young foliage, upper surface: RHS 144A. Young foliage, lower surface: RHS 144B. Mature foliage, upper surface: L*(C)=42.72, a*(C)=−15.77, b*(C)=23.89. Mature foliage, lower surface: L*(C)=49.99, a*(C)=−16.03, b*(C)=26.77.

Flower description:

*Appearance.*—Butterfly-shaped single flowers arranged in umbels borne on a leafless scape. Corolla and calyx similar (tepals), three-parted and fused at the base. Freely flowering, typically four open flowers per scape and eight flowers and flower buds per plant. Flowers last about three or four days each. Flowers persistent. Flowers held perpendicular to the scape.

*Flowering response.*—Plants flower in the spring. Plants typically flower about March 1 to April 1 in Fort Lauderdale, Fla.

*Fragrance.*—Not detected.

*Scape.*—Length: about 44-56 cm. Diameter: About 1.5 cm. Appearance/aspect: Leafless; upright; not fasciated, hollow. Strength: Moderate. Texture: Smooth. Color: 137D.

*Pedicel.*—About 2 to 3 cm long.

*Flower length.*—About 13-14 cm and 15-16 cm.

*Flower diameter.*—About 12-13.5 cm and 14-15 cm.

*Flower depth* (*height*).—About 14-16 cm and 16-18 cm.

*Flower buds.*—Length: about 4 cm. Width: about 1 cm. Shape: Oblanceolate. Color: close to RHS 155D in lower half, RHS 57A in upper half. Rate of flower bud opening: about 2 days each, all flower opening in about 8-10 days.

*Tepals.*—Number: six, in two whorls of 3. Fused and forming tube in proximal 3 cm. Outer whorl: Length: about 12.5-13 cm. Width: about 7-7.5 cm. Shape: broadly ovate. Apex: apiculate. Margin: entire. Texture: Smooth; tepals appear luminous and crystalline. Color: Both surfaces: densely striated RHS 57A, especially upper; with darker markings at the throat (Table 2), and faint white RHS 155D keels, margins irregularly white RHS 155D, outer surfaces more-lightly striated with infusions of green RHS 149B and maroon RHS 178B along the keels. Inner whorl — Shape: ovate, the ventral tepal narrower than the laterals. Apex: apiculate. Margin: Entire. Color: both surfaces: as per outer whorl, but dark markings at throat more pronounced on laterals, irregular white RHS 155D margins (Table 2).

*Throat.*—Green RHS 155C, with lacinate fimbrae.

*Reproductive organs.*—Androecium: Stamen number: Six. Length: about 10-11.2 cm. Filaments the same color as tepals for most of length, green RHS 149B, in proximal 1.5 cm. Anther shape: Elliptic. Anther size: About 8 mm. Anther color: white RHS 155 D. Pollen amount: Moderate. Pollen color: yellow RHS 8C. Gynoecium: Pistil number: One. Pistil length: About 13.5-14 cm. Stigma shape: trifid. Stigma width: about 7 mm. Stigma color: white RHS 155D. Style color: same as tepals for most of length, green RHS 149B in proximal 2 cm. Ovary shape: ellipsoid, ovary length: 22-34 mm, ovary width: 8-11.5 mm, ovary color: RHS 141C.

*Seed.*—Seed development has not been observed.

Chromosome number: 2n=33. Plant is triploid.

Disease resistance: Plants of the new amaryllis appear resistant to Red Scorch Fungus (*Staganospora curtisii*).

Heat tolerance: Plants of the new amaryllis have demonstrated good tolerance to high temperatures about 30 to 35° C.

I claim:

1. A new and distinct cultivar of amaryllis plant (genus *Hippeastrum*) named 'Boca', as illustrated and described.

* * * * *